United States Patent [19]

Carney

[11] 4,064,055
[45] Dec. 20, 1977

[54] AQUEOUS DRILLING FLUIDS AND ADDITIVES THEREFOR

[75] Inventor: Leroy L. Carney, New Caney, Tex.

[73] Assignee: Halliburton Company, Duncan, Okla.

[21] Appl. No.: 691,736

[22] Filed: June 1, 1976

Related U.S. Application Data

[63] Continuation-in-part of Ser. No. 501,000, Aug. 27, 1974, abandoned.

[51] Int. Cl.² .................................................. C09K 7/02
[52] U.S. Cl. ................................. 252/8.5 C; 252/49.3; 252/49.5
[58] Field of Search ................. 252/8.5 C, 8.5 A, 49.3, 252/49.5, 51.5 A

[56] References Cited

U.S. PATENT DOCUMENTS

| 3,014,862 | 12/1961 | Tailleur | 252/8.5 |
|---|---|---|---|
| 3,027,324 | 3/1962 | Rosenberg | 252/8.5 |
| 3,738,992 | 6/1973 | Frump | 252/49.5 X |
| 3,761,410 | 9/1973 | Mondshine et al. | 252/8.5 |

OTHER PUBLICATIONS

Rosenberg et al., Article Journal of Petroleum Technology, vol. 11, Aug. 1959, pp. 195-202.

*Primary Examiner*—Herbert B. Guynn
*Attorney, Agent, or Firm*—Robert S. Nisbett; John H. Tregoning; Thomas R. Weaver

[57] ABSTRACT

The friction created by rotating and reciprocating a drill pipe in a well penetrating a subterranean formation is reduced by including an ester of an oxazolidine derivative in an aqueous drilling fluid or a mixture of said ester and certain alcohols. This ester of an oxazolidine derivative is represented by the following general formula:

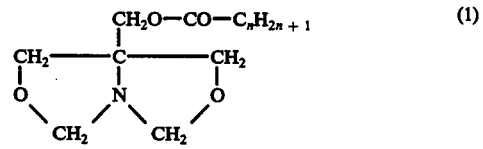

wherein $n$ is a whole integer within the range of about 5 to 20.

12 Claims, No Drawings

AQUEOUS DRILLING FLUIDS AND ADDITIVES THEREFOR

This is a continuation-in-part of Ser. No. 501,000 filed Aug. 27, 1974, now abandoned which is hereby incorporated by reference. All benefits of the prior copending application are herein claimed.

In one method of drilling a well penetrating a subterranean formation, a bit attached to the lower end of a hollow drill pipe extending from the bottom of the well to the surface is rotated. A drilling fluid is circulated down the drill pipe through the bit and to the surface through the annulus defined by the well and drill pipe.

The drilling fluid is generally formulated to serve several important functions. It removes the drilled cuttings from the hole, cools and lubricates the bit and drill pipe, and suspends cuttings and weighting materials when circulation is stopped.

Several additives have been developed to improve the lubrication of the drill pipe and to reduce the friction or drag as the drill pipe is reciprocated or rotated in the well. A reduction in friction reduces the torque required to rotate the drill pipe and the wear and stress on the drill pipe. A drilling fluid formulated with these additives also reduces the danger of having the drill pipe stick as the drill pipe is reciprocated in the well.

It has now been discovered that an oxazolidine derivative can be formulated in several preferred formulations in an aqueous drilling fluid to substantially reduce friction as a drill string is reciprocated or rotated in the well containing the aqueous drilling fluid. Only certain oxazolidine derivatives have been found to be useful as friction reducing additives for aqueous drilling fluid. These derivatives are represented by the following general formula:

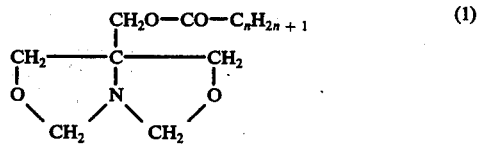

(1)

wherein $n$ is an integer within the range of about 5 to 20 and preferably within the range of about 8 to 17.

The most preferred oxazolidine derivative is represented by the following general formula:

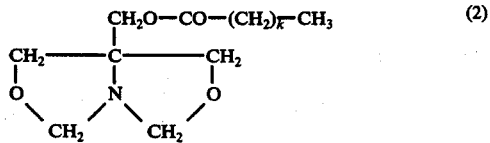

(2)

wherein $k$ is an integer within the range of about 7 to 15. Thus, the preferred acids for preparing the esters contain up to but fewer than 18 carbon atoms and preferably between 9 to 16.

Examples of the esters represented by these oxazolidine derivative formulae include but are not limited to the caproic acid ($C_{10}$), caprylic acid ($C_8$), capric acid ($C_{10}$), lauric acid ($C_{12}$), myristic acid ($C_{14}$), or palmitic acid ($C_{16}$) esters of this oxazolidine derivative.

This oxazolidine derivative is useful at a low concentration in aqueous drilling fluids as a friction reducing agent without interfering with the rheology of the drilling fluid or other additives commonly used for formulating aqueous drilling fluids. The derivative can be used alone or mixed with certain preferred alcohols. Some of the additives commonly used in the formulation of aqueous drilling fluids and contaminants frequently encountered in drilling of fluids are clay and high molecular weight polymers to increase the particle suspending properties of the fluid; ground barite and ground galena to increase the density of the fluid; phosphates, tannins, lignite and lignosulfonate to disperse particles contained in the fluid; starches, celluloses, quar gum and other water soluble polymers to reduce the loss of liquid from the fluid; and surfactants as wetting agents in the fluid.

These derivatives or esters of oxazolidine or mixture of alcohol and ester are useful in aqueous drilling fluids for reducing friction at concentrations as low as about 0.2 pound per 42-gallon barrel of aqueous drilling fluid. At concentrations lower than about 0.2 pound per barrel, insufficient friction reduction is noted when using this derivative. The maximum concentration of this derivative useful as a friction reducing additive is about 5 pounds per 42-gallon barrel of aqueous drilling fluid for economy and to minimize effects on rheology. This oxazolidine derivative is preferably used in aqueous drilling fluids to reduce friction at about 0.5 to 2 pounds per barrel of aqueous drilling fluid. It should also be noted that this oxazolidine derivative can be formulated with other friction reducing agents such as diphosphate esters of aliphatic carboxylic acids, vegetable oils and asphalt particles. In combination with other friction reducing agents, this oxazolidine derivative could be used at lower concentrations to obtain comparable reductions in friction.

The oxazolidine derivatives or esters which have been found useful as drilling fluid lubricants can be mixed with certain alcohols to produce a composition which is stable in the presence of contaminants, other additives and to temperatures up to and above about 150° F. This mixture also has improved foam suppression properties. Thus, the mixed composition is stable to contaminants normally encountered in drilling such as alkali and alkaline earth metals including calcium, sodium and potassium. The polyvalent metals are frequently encountered or added as salts which have limited solubility, yet significantly affect and even precipitate or flocculate drilling fluid components. For example, the contaminants could come from strata containing salt, salt water, calcium clays, etc., or the salts could be added as lime, clay, clay inhibiting salt, etc. Thus, the mere presence of or exposure of the drilling mud to these metals, salts or contaminants is frequently all that is necessary to detrimentally affect the drilling mud or its components. The compositions of this invention have proved to be both chemically and thermally stable, as well as superior lubricants in the presence of the high surface area of suspended solids in the drilling mud and of the bore hole.

The preferred esters can be mixed with certain alcohols to enhance the lubricating properties, further minimize effects on drilling fluid rheology and modify these characteristics upon heat aging. The esters can be mixed with up to 95% by weight of these alcohols but preferably contain about 30%–70% or 40%–60% alcohol in the mixture or about equal amounts (50%) of ester and alcohol. The preferred alcohols are linear or substantially linear, low molecular weight alcohols having 1–8 carbon atoms. The higher molecular weight $C_3$–$C_8$ alcohols are preferred within this class for more uniform properties with varying time and temperature.

The lubricating properties of compositions of this invention are possessed only by certain esters and certain ester alcohol mixtures. These unexpected properties of lubricity and stability suitable for drilling fluids are also accompanied by unexpected advantageous effects on the rheology of the drilling mud which is essential; or at least, the absence of detrimental effects on rheology is essential.

The following examples are presented to illustrate specific aspects of the use of this oxazolidine derivative in aqueous drilling fluids to reduce friction.

EXAMPLE I

The test represented by Table 1 illustrates the rheological properties, gel strengths and friction reducing properties of an aqueous drilling fluid containing the lauric acid ester of an oxazolidine derivative. This oxazolidine derivative is represented by the following formula:

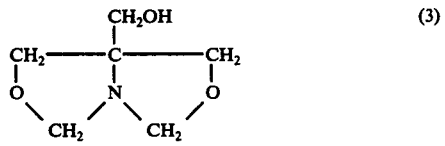

(3)

The lauric acid ester of this oxazolidine derivative is represented by the following formula:

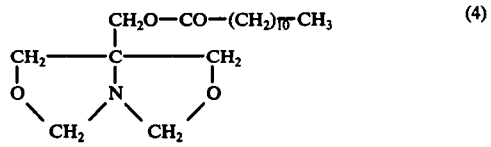

(4)

The aqueous drilling fluid, also referred to as base mud, is formulated by mixing 0.87 pound of sodium chloride, 1.75 pounds of calcium carbonate, 16 pounds of sodium bentonite and 34 pounds of calcium bentonite with water per barrel or 42 gallons to produce an aqueous drilling fluid having a density of about 9 pounds per U.S. gallon and a pH of about 8.3. The aqueous drilling fluid containing the oxazolidine derivative and the lauric acid ester of this derivative are formulated with about one pound of these oxazolidine derivatives per 42-gallon barrel (i.e. one ppb) of the aqueous drilling fluid.

The plastic viscosity, yield points and gel strengths are measured with a Fann Instrument Company Model 35A rotational viscometer (i.e. VG meter). The lubricating properties of the drilling fluid are measured with an American Petroleum Institute standard lubricity tester. Tests are run according to standard methods such as API Method B-B which is incorporated herein by reference. The lubricity tester is calibrated with fresh water and a base mud or aqueous drilling fluid for each set of samples. A metal block and a rotating ring are immersed in each mud sample. The block is pressed against the rotating ring by a torque wrench. The pressure or drag between the block and ring is maintained constant at about 40–42 foot pounds per square inch by varying the torque applied to the block. The drag is measured by a meter in the circuit of the electric motor driving the ring. The torque applied to the block is reported as the load in pounds as indicated on the torque wrench. Test results for the first set of samples are reported in Table 1.

The plastic viscosity and yield point measurements reported on Table 1 are made immediately after mixing the oxazolidine derivative or its lauric acid ester with the aqueous drilling fluid. The gel strength measurements are made after the mixtures are quiescent for about ten minutes, and the lubricity is measured after the mixtures have been in the lubricity tester with the ring moving through the aqueous drilling fluid for about ten minutes with sufficient torque being applied to the block to produce a drag or meter reading of about 42.

The test results reported on Table 1 indicate that the lauric acid ester of this oxazolidine derivative significantly reduces the friction between one body moving in respect to another body. These tests also indicate that the lauric acid ester of this oxazolidine derivative has little effect on such properties as the viscosity, yield point or gel strength of an aqueous drilling fluid.

Table 1

| | | Properties of Aqueous Drilling Fluid Containing The Lauric Acid Ester of Oxazolidine Derivative | | | | | | | | |
|---|---|---|---|---|---|---|---|---|---|---|
| | | VG Meter Readings | | | | Gel Strength (lbs/100 sq. ft.) | | Load (lbs) - Minutes | | |
| Sample | Additive | 600 | 300 | PV | YP | 10 Sec. | 10 Min. | Initial | 5 | 10 | 15 |
| 1 | Base Mud[a] | 28 | 20 | 8 | 12 | 15 | 23 | 190 | 180 | 180 | 160 |
| 2 | LAE-OXT[d] | 39 | 28 | 11 | 17 | 16 | 27 | 400 | 600[j] | 600 | 600 |
| 3 | OXT[i] | 27 | 20 | 7 | 13 | 15 | 24 | 190 | 180 | 180 | 160 |

Table 2A
Tests After Samples Hot Rolled at 150° F For 4 Hours

| 1 | Base Mud | 198 | 160 | 38 | 122 | 130 | 225 | 110 | 100 | 100 | 100 |
|---|---|---|---|---|---|---|---|---|---|---|---|
| 2 | LAE-OXT | 168 | 140 | 28 | 112 | 110 | 155 | 130 | 150 | 180 | 180 |
| 3 | PAE-OXT[e] | 190 | 139 | 51 | 88 | 85 | 165 | 130 | 180 | 200 | 220 |
| 4 | SAE-OXT[f] | 247 | 220 | 27 | 193 | 160 | 155 | 130 | 170 | 200 | LU[b] |
| 5 | TAE-OXT[g] | 230 | 195 | 35 | 160 | 140 | 180 | 220 | LU[c] | LU | LU |

Table 2B
Ambient Temperature Tests

| 1 | Base Mud | 171 | 140 | 31 | 109 | 115 | 210 | | 95 | 95 | 95 |
|---|---|---|---|---|---|---|---|---|---|---|---|
| 2 | LAE-OXT | 160 | 130 | 30 | 100 | 100 | 180 | | 200 | 210 | 210 |
| 3 | PAE-OXT | 161 | 127 | 34 | 93 | 95 | 165 | | LU[h] | LU | LU |
| 4 | SAE-OXT | 150 | 120 | 30 | 90 | 95 | 165 | | LU[h] | LU | LU |

Table 1-continued

Properties of Aqueous Drilling Fluid Containing
The Lauric Acid Ester of Oxazolidine Derivative

| Sample | Additive | VG Meter Readings | | | | Gel Strength (lbs/100 sq. ft.) | | Load (lbs) - Minutes | | | |
|---|---|---|---|---|---|---|---|---|---|---|---|
| | | 600 | 300 | PV | YP | 10 Sec. | 10 Min. | Initial | 5 | 10 | 15 |
| 5 | TAE-OXT | 165 | 132 | 33 | 99 | 97 | 146 | | 200 | 150 | 150 |

*Base Mud is the same as the aqueous drilling fluid with no friction reducing additive.
*In less than 15 minutes at a load of 200 pounds on the block, the block and ring seized to prevent movement of the ring.
*In less than 5 minutes at a load of 220 pounds on the block, the block and ring seized to prevent movement of the ring.
*LAE-OXT is lauric acid ($C_{12}$) ester of oxazolidine T in base mud.
*PAE-OXT is pelargonic acid ($C_9$) ester.
*SAE-OXT is stearic acid ($C_{18}$) ester.
*TAE-OXT is tall oil acid ($C_{18}$) ester.
*LU means locked up or ring and block seized to stop movement of ring.
*OXT is 1 ppb of a 50% aqueous solution of oxazolidine T.
*Maximum load that could be applied with equipment.

EXAMPLE II

The tests represented by Table 2A and 2B illustrate the rheological properties, gel strength and friction reducing properties of an aqueous drilling fluid containing various esters of the oxazolidine derivative shown in Example I. The aqueous drilling fluid was formulated by the procedure described in Example I with the esters being included in the aqueous drilling fluid at one pound of the oxazolidine derivative ester of the acid indicated on Table 2A and 2B per 42-gallon barrel of aqueous drilling fluid. The tests reported on Table 2A were conducted by the procedures described in Example I with the aqueous drilling fluids being hot rolled or cured with agitation for about four hours at 150° F prior to conducting such tests. Test results reported in Table 2B were conducted on samples maintained at ambient temperature.

EXAMPLE III

The tests represented by Table 3 illustrate the rheological properties, gel strength and friction reducing properties of an aqueous drilling fluid containing various concentrations of the lauric acid ester of the oxazolidine derivative shown in Example I. The aqueous drilling fluid was formulated by the procedure described in Example I with the oxazolidine derivative being included in the aqueous drilling fluid at the concentration indicated on Table 3. The tests represented by Table 3 were conducted by the procedures described in Example I.

These tests indicate that these oxazolidine derivatives can be included in an aqueous drilling fluid at concentrations as high as about 5 pounds per 42-gallon barrel without significantly altering the rheological characteristics or gel strength of the aqueous drilling fluid. However, it is noted that concentrations of the derivative above about 2 pounds per 42-gallon barrel do increase the yield point of the aqueous drilling fluid. It is also noted that concentrations of the derivative above about 2 pounds per 42-gallon barrel do not further reduce the friction to the extent that the use of such higher concentrations would be justified.

Table 3

Properties of Aqueous Drilling Fluid Mixed With
Various Concentrations of the Lauric Acid Ester
of Oxazolidine Derivative

| Lubtricant (lbs./42-gal. bbl.) | Plastic Viscosity (cps) | Yield Point (lbs./100 sq. ft.) | Gel Strength at 10 min. (lbs./100 sq. ft.) | Load at 10 min. (lbs.) |
|---|---|---|---|---|
| None | 10 | 32 | 75 | 103 |
| 0.2 | 11 | 31 | 37 | 130 |
| 0.5 | 14 | 29 | 39 | 200 |
| 1 | 15 | 31 | 42 | 325 |
| 2 | 15 | 35 | 46 | 400 |
| 3 | 13 | 58 | 54 | 430 |
| 4 | 15 | 60 | 56 | 425 |
| 5 | 18 | 84 | 62 | 460 |

EXAMPLE IV

Samples of drilling mud are prepared and tested as described in Example I, containing various amounts of an additive (i.e. DPE) used for lubricity and are compared to samples using a preferred oxazolidine T ester (i.e. lauric acid ester, LAE-OXT). Test results are listed in Table 4. It will be noted that even at ¼ ppb the preferred LAE-OXT additive is superior in lubricating properties to all three samples containing the DPE additive with little effect on the viscosity and gel properties.

Table 4

| Sample | Additive | VG Meter Readings | | | | Gel Strength (lbs/100 sq. ft.) | | Load (lbs) - Minutes | | | |
|---|---|---|---|---|---|---|---|---|---|---|---|
| | | 600 | 300 | PV | YP | 10 Sec. | 10 Min. | Initial | 5 | 10 | 15 |
| 1 | Base Mud<sup>a</sup> | 31 | 22 | 9 | 13 | 17 | 30 | 80 | 40 | 50 | 50 |
| 2 | ¼ pps DPE<sup>b</sup> | 32 | 23 | 9 | 14 | 16 | 27 | 80 | 60 | 60 | 60 |
| 3 | ½ ppb DPE | 33 | 23 | 10 | 13 | 16 | 27 | 80 | 80 | 70 | 70 |
| 4 | 1 ppb DPE | 34 | 24 | 10 | 14 | 16 | 28 | 90 | 80 | 90 | 80 |
| 5 | ¼ ppb LAE-OXT<sup>c</sup> | 34 | 26 | 8 | 18 | 21 | 33 | 110 | 100 | 100 | 100 |
| 6 | ½ ppb LAE-OXT | 36 | 27 | 9 | 18 | 21 | 33 | 110 | 100 | 100 | 100 |
| 7 | 1 ppb LAE-OXT | 38 | 27 | 11 | 16 | 21 | 33 | 110 | 120 | 130 | 140 |

*Base Mud is the same as the aqueous drilling fluid with no friction reducing additive.
*DPE is by weight 1% Neodol, 1% LAE-OXT, 5% diphosphate ester of a long chain ethoxylated alkyl with 10% triethanolamine and 73% water. Neodol is a mixture of $C_{12}$-$C_{15}$ linear primary alcohols.
*LAE-OXT is the lauric acid ester of oxazolidine T.

EXAMPLE V

Samples are prepared and tested as in Example I containing various lubricating additives. The additives are used in a concentration of 1 ppb unless indicated otherwise. Load capacity of each sample is tabulated in Tables 5A and 5B. The samples reported in Table 5B were heat aged with agitation or hot rolled at 150° F for 16 hours and then tested at ambient temperature. The tests show that samples containing the preferred lauric acid-oxazolidine T ester alone or mixed with a $C_1$-$C_8$ alkyl alcohol consistently has superior lubricating properties initially and after aging at about 150° F, while the other additives show poor initial values and/or significant loss of load bearing characteristics at temperatures of about 150° F or higher.

Table 5A
Load Capacity at Ambient Temperature (lbs.)

| Sample | Material | Initial | 5 | 10 | 15 | 20 | 25 | 30 |
|---|---|---|---|---|---|---|---|---|
| A | DPE[a] | 235 | 250 | 135 | 240 | 265 | 280 | 265 |
| B | CO[b] | 320 | 360 | 420 | 470 | 430 | 500 | 500 |
| C | ST[c] | 120 | 145 | 225 | 240 | 260 | 260 | 260 |
| D | CD[d] | 260 | 275 | 240 | 300 | 310 | 310 | 320 |
| E | CA[e] | 215 | 250 | 270 | 275 | 285 | 285 | 320 |
| F | Base Mud | 220 | 240 | 230 | 210 | 240 | 260 | 260 |
| G | OXT-OCT[f] | 425 | 415 | 470 | 490 | 490 | 490 | 490 |
| H | OXT[g] | 330 | 305 | 330 | 350 | 370 | 335 | 335 |
| I | OXT-ET[h] | 275 | 320 | 370 | 380 | 405 | 405 | 425 |
| J | OXT-ME[i] | 280 | 350 | 415 | 430 | 440 | 440 | 450 |
| K | OXT-ISO[j] | 290 | 350 | 370 | 375 | 375 | 375 | 410 |

Table 5B
Load Capacity After Hot Rolling at 150° F (lbs) for 16 Hours

| A | DPE | 240 | 270 | 270 | 270 | 270 | 270 | 270 |
|---|---|---|---|---|---|---|---|---|
| B | CO | 180 | 250 | 280 | 280 | 290 | 300 | 300 |
| C | ST | 250 | 260 | 260 | 250 | 250 | 285 | e |
| D | CD | 150 | 245 | 260 | 285 | 290 | 290 | 290 |
| E | CA | 140 | 235 | 250 | 250 | 250 | 250 | 250 |
| F | Base Mud | 170 | 200 | 210 | 165 | 165 | 165 | 165 |
| G | OXT-OCT | 320 | 400 | 450 | 370 | 370 | 410 | 410 |
| H | OXT | 185 | 330 | 360 | 400 | 430 | 450 | 480 |
| I | OXT-ET | 210 | 250 | 290 | 290 | 340 | 340 | 350 |
| J | OXT-ME | 240 | 330 | 360 | 375 | 375 | 375 | 375 |
| K | OXT-ISO | 265 | 240 | 240 | 290 | 310 | 320 | 320 |

[a]DPE is by weight 1% Neodol, 1% LAE-OXT, 5% diphosphate ester of a long chain ethoxylated alkyl with 10% triethanolamine and 73% water. Neodol is a mixture of $C_{12}$-$C_{15}$ linear primary alcohols.
[b]Emulsified cottonseed oil.
[c]3½% potassium stearate, 3½% sodium stearate with blue dye in water.
[d]Cedar oil.
[e]Castor oil in nonyl alcohol.
[f]2 ppb 50% oxazolidine T ester with 50% octanol.
[g]Oxazolidine T ester.
[h]2 ppb 50% oxazolidine T ester with 50% ethanol.
[i]2 ppb 50% oxazolidine T ester with 50% methanol.
[j]50% oxazolidine T ester with 50% isopropanol.

It is to be understood that the description and foregoing examples are given for the purposes of illustrating and explaining the invention, and that suitable variations may be made within the scope of the appended claims without departing from the invention.

What is claimed is:

1. An aqueous drilling fluid comprising water, clay and a friction reducing composition present in an amount of from about 0.2 pounds per barrel up to about 5 pounds per barrel of drilling fluid wherein said friction reducing composition comprises an ester of an acid and an oxazolidine derivative, said ester consisting essentially of a derivative represented by the following formula:

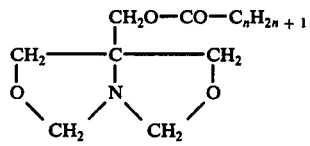

wherein $n$ is an integer in the range of about 8 to 16.

2. An aqueous drilling fluid of claim 1 wherein said acid is caproic acid, caprylic acid, capric acid, lauric acid, myristic acid, palmitic acid, pelargonic acid or mixtures thereof.

3. An aqueous drilling fluid comprising water, clay and a friction reducing composition which is stable in said drilling fluid at temperatures above about 150° F, is stable in the presence of drilling fluid additives and contaminants and which substantially reduces foaming and drag comprising a mixture of up to 95% by weight of at least one linear alkyl alcohol having about three to eight carbon atoms per molecule with an ester of an acid and an oxazolidine derivative, said ester consisting essentially of a derivative represented by the formula:

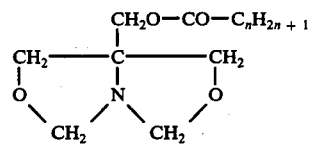

wherein $n$ is a whole integer in the range of about 8 to 16, wherein said ester is present in an amount of about 0.2-5 pounds per barrel of said drilling fluid.

4. A drilling fluid of claim 3 wherein said composition comprises a mixture of about 30%-70% of at least one linear alcohol with said ester.

5. A drilling fluid of claim 3 wherein said composition comprises a mixture of about 40%-60% of at least one linear alcohol with said ester, wherein said acid is caproic acid, caprylic acid, capric acid, lauric acid, myristic acid, palmitic acid, pelargonic acid or mixtures thereof.

6. A drilling fluid of claim 3 wherein said acid is lauric acid, pelargonic acid or combinations thereof.

7. A method of drilling a well penetrating a subterranean formation using an aqueous drilling fluid comprising water and clay, said method comprising rotating a bit in contact with the bottom of said said well and attached to the lower end of a hollow drill pipe extending from the bottom of said well to the surface while circulating an aqueous drilling fluid comprising water, clay and an effective amount of a friction reducing composition downwardly through the drill pipe and upwardly through the annulus of said well, said friction reducing composition comprising an ester of an acid and an oxazolidine derivative, said ester consisting essentially of a derivative represented by the following formula:

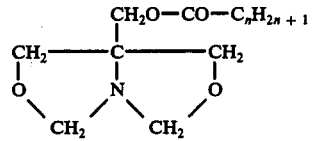

wherein $n$ is an integer in the range of about 8-16.

8. A method of claim 7 wherein said acid is caproic acid, caprylic acid, capric acid, lauric acid, myristic acid, palmitic acid, pelargonic acid or mixtures thereof.

9. A method of claim 7 wherein said acid is lauric acid, pelargonic acid or combinations thereof.

10. A method of claim 7 wherein said friction reducing composition comprises a mixture of up to about 95% by weight of at least one linear alkyl alcohol having three to eight carbon atoms with said ester.

11. A method of claim 10 wherein said friction reducing composition comprises a mixture of about 30%-70% by weight of at least one linear alcohol with said ester, and wherein said acid is caproic acid, caprylic acid, capric acid, lauric acid, myristic acid, palmitic acid, pelargonic acid or mixtures thereof.

12. A method of claim 10 wherein said friction reducing composition comprises a mixture of about 40%-60% of at least one linear alkyl alcohol with said ester, and wherein said acid is lauric acid, pelargonic acid or combinations thereof.

* * * * *